(12) United States Patent
Godwin et al.

(10) Patent No.: US 12,297,491 B2
(45) Date of Patent: May 13, 2025

(54) PRIMER EXTENSION TARGET ENRICHMENT AND IMPROVEMENTS THERETO INCLUDING SIMULTANEOUS ENRICHMENT OF DNA AND RNA

(71) Applicant: Roche Sequencing Solutions, Inc., Pleasanton, CA (US)

(72) Inventors: Brian Christopher Godwin, Livermore, CA (US); Sedide Ozturk, Pleasanton, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 97 days.

(21) Appl. No.: 18/046,058

(22) Filed: Oct. 12, 2022

(65) Prior Publication Data
US 2023/0357830 A1 Nov. 9, 2023

Related U.S. Application Data

(63) Continuation of application No. 16/549,962, filed on Aug. 23, 2019, now Pat. No. 11,499,180, which is a continuation of application No. PCT/EP2018/055579, filed on Mar. 7, 2018.

(60) Provisional application No. 62/468,569, filed on Mar. 8, 2017.

(51) Int. Cl.
| | | |
|---|---|---|
| *C12P 19/34* | (2006.01) | |
| *C12Q 1/6806* | (2018.01) | |
| *C12Q 1/6855* | (2018.01) | |
| *C12Q 1/6869* | (2018.01) | |

(52) U.S. Cl.
CPC ......... *C12Q 1/6855* (2013.01); *C12Q 1/6806* (2013.01); *C12Q 1/6869* (2013.01)

(58) Field of Classification Search
CPC .................................................. C12Q 1/6869
See application file for complete search history.

(56) References Cited

U.S. PATENT DOCUMENTS

| | | |
|---|---|---|
| 7,393,665 B2 | 7/2008 | Brenner |
| 8,168,385 B2 | 5/2012 | Brenner |
| 8,481,292 B2 | 7/2013 | Casbon et al. |
| 8,685,678 B2 | 4/2014 | Casbon et al. |
| 8,722,368 B2 | 5/2014 | Casbon et al. |
| 8,932,831 B2 | 1/2015 | Korfhage et al. |
| 9,315,863 B2 | 4/2016 | Nadeau |
| 9,546,399 B2 | 1/2017 | Amorese et al. |
| 10,421,999 B2 | 9/2019 | Donahue et al. |
| 10,590,471 B2 | 3/2020 | Godwin |
| 2004/0110153 A1 | 6/2004 | Dong et al. |
| 2013/0231253 A1 | 9/2013 | Amorese et al. |
| 2013/0303461 A1 | 11/2013 | Iafrate et al. |
| 2015/0119261 A1 | 4/2015 | Richard |
| 2015/0133312 A1 | 5/2015 | Bielas et al. |
| 2015/0211050 A1 | 7/2015 | Lafrate et al. |
| 2016/0201124 A1 | 7/2016 | Donahue et al. |
| 2016/0203259 A1 | 7/2016 | Scolnick et al. |
| 2016/0222427 A1 | 8/2016 | So et al. |
| 2017/0016056 A1 | 1/2017 | Tan et al. |
| 2018/0080021 A1 | 3/2018 | Reuter et al. |
| 2019/0071732 A1 | 3/2019 | Jia et al. |
| 2020/0024644 A1 | 1/2020 | Wang et al. |

FOREIGN PATENT DOCUMENTS

| | | |
|---|---|---|
| CN | 103589803 A | 2/2014 |
| CN | 104195148 A | 12/2014 |
| CN | 110628880 A | 12/2019 |
| WO | 2001/032887 A1 | 5/2001 |
| WO | 2015/121236 A1 | 8/2015 |
| WO | 2015/148219 A1 | 10/2015 |
| WO | 2016/118085 A1 | 7/2016 |
| WO | 2016/118719 A1 | 7/2016 |
| WO | 2017/021449 A1 | 2/2017 |

OTHER PUBLICATIONS

Berka, Jan et al., Provisional Patent Application No. 62/344,330, filed Jun. 1, 2016, Immuno-Pete, 34 pp.
Godwin, Brian et al., US Provisional Patent Application, Primer Extension Target Enrichment, filed Jul. 12, 2016, 36 pp.
Guido, Nicholas et al., Improved PCR Amplifications of Broad Spectrum GC DNA Templates, PLOS ONE, vol. 11, No. 6, e0156478, 11 pp., 2016.
Hopple, Gordon D. et al., Gel-seq: whole-genome and transcriptome sequencing by simultaneous low-input DNA and RNA library preparation using semi-permeable hydrogel barriers, Lab Chip, vol. 17, No. 15, pp. 2619-2630, 2017.
International Search Report and Written Opinion, dated Apr. 24, 2018, in corresponding PCT/EP2018/055579 filed Mar. 7, 2018, pp. 1-10.
Liu, Qiang and Sommer, Steve S., Subcycling-PCR for Multiplex Long-Distance Amplification of Regions with High and Low GC Content: Application to the Inversion Hotspot in the Factor VIII Gene, BioTechniques, vol. 25, No. 6, pp. 1022-1028, 1998.
Mertens, Fredrik et al., The emerging complexity of gene fusions in cancer, Nature Reviews Cancer, vol. 15, pp. 371-381, 2015.
Newman, Aaron M. et al., An ultrasensitive method for quantitating circulating tumor DNA with broad patient coverage, Nature Medicine, vol. 20, No. 5, pp. 548-554, 2014.
Newman, Aaron M. et al., Integrated digital error suppression for improved detection of circulating tumor DNA, Nature Biotechnology, vol. 34, No. 5, pp. 547-555, 2016.
Reuter, Jason A. et al., Simul-seq: combined DNA and RNA sequencing for whole-genome and transcriptome profiling, Nature Methods, vol. 13, No. 11, pp. 953-961, 2016.

*Primary Examiner* — Kenneth R Horlick
(74) *Attorney, Agent, or Firm* — Charney IP Law LLC; Thomas M. Finetti

(57) ABSTRACT

The present invention is a method and compositions for primer extension target enrichment of nucleic acids and improvements thereto including simultaneously enriching for RNA and DNA and optionally sequencing the enriched products.

4 Claims, 10 Drawing Sheets

FIGURE 7
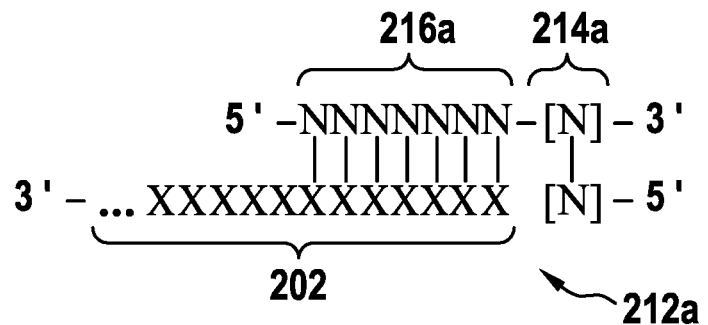
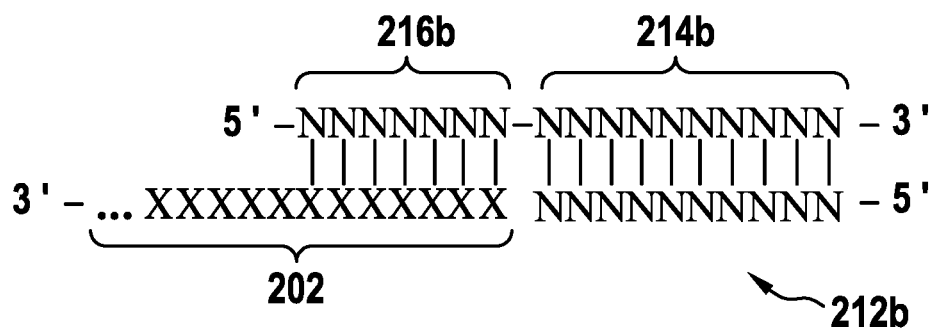
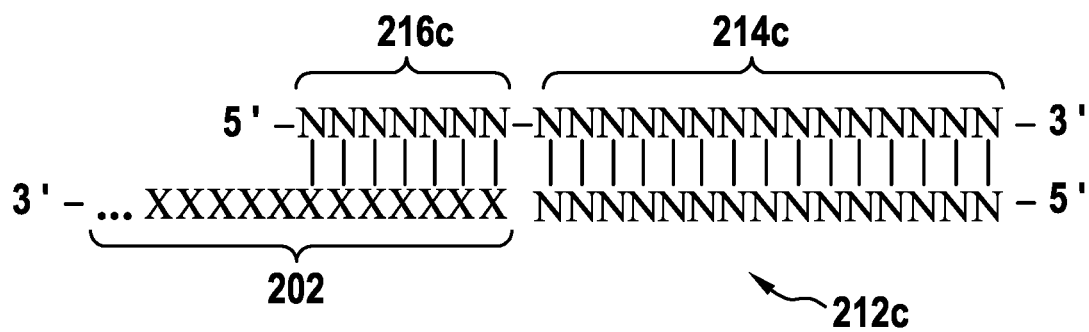

PRIMER EXTENSION TARGET ENRICHMENT AND IMPROVEMENTS THERETO INCLUDING SIMULTANEOUS ENRICHMENT OF DNA AND RNA

CROSS REFERENCE TO RELATED APPLICATIONS

The pending application is a continuation of U.S. patent application Ser. No. 16/549,962 filed on Aug. 23, 2019, now U.S. Pat. No. 11,499,180, which application is a continuation of International Application No. PCT/EP2018/055579 filed on Mar. 7, 2018, which application claims the benefit of the filing date of U.S. Provisional Patent Application No. 62/468,569 filed on Mar. 8, 2017, the disclosures of which are hereby incorporated by reference herein in their entireties.

FIELD OF THE INVENTION

The invention relates to the field of nucleic acid sequencing. More specifically, the invention relates to the field of enriching rare nucleic acid targets for sequencing.

BACKGROUND OF THE INVENTION

Sample preparation for high-throughput sequencing typically involves an enrichment step that increases the ratio of nucleic acids containing the target sequence to non-target nucleic acids in a sample. Sequence-based enrichment techniques known in the art include hybrid capture, PCR amplification, primer extension target enrichment (PETE). Primer-based target enrichment methods involve one or more rounds of synthesis of a copy strand. Some clinical applications of DNA sequencing aim to detect very rare targets, e.g., cell-free tumor DNA (ctDNA) present in the blood of cancer. The tumor DNA, distinguished by mutations is present at concentrations as low as several copies per mL of a typical blood sample. There is a need to reliably detect such rare target sequences utilizing as little sample material from a patient as possible.

SUMMARY OF THE INVENTION

In one embodiments, the invention is a method of enriching a target polynucleotide from a sample, the method comprising: providing a sample comprising the target polynucleotide; hybridizing a first target-specific primer to the target polynucleotide wherein the primer comprises a target-binding region and a region of complementarity to an adaptor; extending the hybridized target-specific primer with a DNA polymerase to form a primer extension product; contacting the sample with the adaptor comprising a longer strand with a 5'-overhang and a shorter strand wherein 5'-overhang comprises a region complementary to the region in the target-specific primer, and the shorter strand comprises a universal priming site; hybridizing the adaptor to the primer extension product; ligating one strand of the adaptor to the primer extension product to form a ligation product; hybridizing a second target-specific primer to the primer extension product wherein the second target-specific primer comprises a target-binding site and a universal priming site; amplifying the ligation product utilizing primers hybridizing to the universal priming sites. In some embodiments, primer annealing and extension steps or primer annealing and amplifying steps are performed simultaneously. In some embodiments, the method further comprises purification step removing the target-specific primer or the adaptor. The purification may be selected from enzymatic digestion, size-exclusion based purification and affinity-based purification.

In some embodiments, amplifying is with a DNA polymerase with a hot-start capability.

In some embodiments, the length of the shorter strand of the adaptor is shorter or equal to 1.5× the length of 5'-overhang. In some embodiments the adaptor comprises an extension block at 3'-end. The block may comprise a 3'- or a 2'-phosphate group.

In some embodiments, amplifying comprises a subcycling thermocycling profile.

In some embodiments at least one of the first and second target specific primers comprises a barcode such as a unique molecular barcode (UID) and a sample barcode (SID).

In some embodiments amplifying in step h) comprises a digital droplet PCR.

More detailed, the present invention provides a method of enriching a target polynucleotide from a sample, the method comprising:
a) providing a sample comprising the target polynucleotide;
b) hybridizing a first target-specific primer to the target polynucleotide wherein the primer comprises a target-binding region and a region of complementarity to an adaptor;
c) extending the hybridized target-specific primer with a DNA polymerase to form a primer extension product;
d) contacting the sample with the adaptor comprising a longer strand with a 5'-overhang and a shorter strand wherein 5'-overhang comprises a region complementary to the region in the target-specific primer, and the shorter strand comprises a universal priming site;
e) hybridizing the adaptor to the primer extension product;
f) ligating one strand of the adaptor to the primer extension product to form a ligation product;
g) hybridizing a second target-specific primer to the primer extension product wherein the second target-specific primer comprises a target-binding site and a universal priming site;
h) amplifying the ligation product utilizing primers hybridizing to the universal priming sites.

Steps b) and c) may be performed simultaneously. Steps g) and h) are performed simultaneously. The method may further comprising a purification step removing the target-specific primer after step c). A purification step may also be used to remove the adaptor after step e). Purification may be selected from enzymatic digestion, size-exclusion based purification and affinity-based purification. The amplification in step h) may be executed by a DNA polymerase with a hot-start capability.

The length of the shorter strand of the adaptor may be shorter or equal to 1.5× the length of 5'-overhang. The adaptor may comprises an extension block at 3'-end which is preferably a 3'- or a 2'-phosphate group.

The amplification step h) may comprise a subcycling thermocycling profile. At least one of the first and second target specific primers may comprise a barcode which may be a unique molecular barcode (UID) or a sample barcode (SID). Step h) may be performed as a digital droplet PCR.

The present invention also provides a method of enriching a target polynucleotide from a sample, the method comprising:

a) providing a sample comprising the target polynucleotide in both single stranded RNA and double stranded DNA form;
b) hybridizing a first target-specific primer to the single-stranded RNA form of the target polynucleotide wherein the primer comprises a target-binding region and a region of complementarity to an adaptor;
c) extending the hybridized first target-specific primer with a reverse transcriptase to form a double-stranded RNA-DNA hybrid comprising an RNA strand and a first primer extension product;
d) subjecting the sample to double stranded nucleic acid denaturation conditions;
e) hybridizing a second target-specific primer to the denatured DNA wherein the primer comprises a target-binding region and a region of complementarity to the adaptor;
f) extending the hybridized second target-specific primer with a DNA polymerase to form a second primer extension product;
g) contacting the sample with the adaptor comprising a longer strand a shorter strand wherein the longer strand comprises a region complementary to the region in the target-specific primer, and the shorter strand comprises a universal priming site;
h) hybridizing the adaptor to the first and second primer extension products;
i) ligating one strand of the adaptor to the first and the second primer extension products to form ligation products;
j) hybridizing the third target-specific primer to the first primer extension product and a fourth primer to the second primer extension product wherein the third and fourth target-specific primers comprise a target-binding site and a universal priming site; and
k) amplifying the ligation products utilizing primers hybridizing to the universal priming sites.

The first and second target-specific primers may comprise unique molecular barcodes. The first target-specific primer may be the same as the second target-specific primer. Alternatively, the first target-specific primer may be different from the second target-specific primer but targets the same gene. The third target-specific primer may be the same as the fourth target specific primer. In a particular embodiment, the first target-specific primer is the same as the second target-specific primer but the third target-specific primer differs from the fourth target-specific primer.

The method may further comprise a step of removing the RNA from the RNA-DNA hybrid after step c). Also the method may further comprise a step of removing unused primers from the sample prior to contacting the sample with the adaptor in step g) or a step of removing unused primers from the sample prior to amplifying in step k). The method may also comprise a step of removing single stranded nucleic acids after steps c) and f). The DNA polymerase in step f) may be a thermostable polymerase with a hot-start capability.

The present invention also comprises a method of sequencing a target polynucleotide from a sample, the method comprising the steps of:
a) providing a sample comprising the target polynucleotide in both single stranded RNA and double stranded DNA form;
b) hybridizing a first target-specific primer to the single-stranded RNA form of the target polynucleotide wherein the primer comprises a target-binding region and a region of complementarity with an adaptor;
c) extending the hybridized first target-specific primer with a reverse transcriptase to form a double-stranded RNA-DNA hybrid comprising an RNA strand and a first primer extension product;
d) subjecting the sample to double stranded nucleic acid denaturation conditions;
e) hybridizing the second target-specific primer to the denatured DNA;
f) extending the hybridized second target-specific primer, wherein the primer comprises a target-binding region and a region of complementarity with an adaptor with a DNA polymerase to form a second primer extension product;
g) contacting the sample with the adaptor comprising a longer strand a shorter strand wherein the longer strand comprises a region complementary to the region in the first and second target-specific primers, and the shorter strand comprises a universal priming site;
h) hybridizing the adaptor to the first and second primer extension products;
i) ligating one strand of the adaptor to the first and the second primer extension products to form ligation products;
j) hybridizing the third target-specific primer to the first primer extension product and the fourth target-specific primer to the second primer extension product wherein the third and fourth target-specific primers comprise a target-binding site and a universal priming site;
k) amplifying the ligation products utilizing primers hybridizing to the universal priming sites;
l) sequencing the amplified ligation products from step k).

The universal primer may be used as a sequencing primer. Alternatively, the third and fourth target-specific primers further comprise a sequencing primer binding site. Still alternatively, the adaptor further comprises a sequencing primer binding site. The adaptor may also comprise a barcode, which may be a sample-identification barcode.

In a particular embodiment, if the universal primer is also used as a sequencing primer, a gene fusion in a sample may be detected. In this case, a target polynucleotide from a sample is processed and sequenced in such a way that the first and second target-specific primers are the same but the third and fourth target-specific primers are different.

The present invention further comprises a method of enriching a target polynucleotide from a sample, the method comprising:
a) providing a sample comprising the target polynucleotide in both single stranded RNA and double stranded DNA form;
b) hybridizing a first target-specific primer to the single-stranded RNA form of the target polynucleotide wherein the primer comprises a target-binding region;
c) extending the hybridized first target-specific primer with a reverse transcriptase to form a double-stranded RNA-DNA hybrid comprising an RNA strand and a first primer extension product;
d) subjecting the sample to double stranded nucleic acid denaturation conditions;
e) hybridizing a second target-specific primer to the denatured DNA wherein the primer comprises a target-binding region and a region of complementarity to an adaptor;
f) hybridizing a third target-specific primer to the first primer extension product wherein the primer comprises a target-binding region and a region of complementarity to the adaptor;

g) extending the hybridized second and third target-specific primers with a DNA polymerase to form a second and third primer extension products;

h) contacting the sample with the adaptor comprising a longer strand a shorter strand wherein the longer strand comprises a region complementary to the region in the target-specific primers, and the shorter strand comprises a universal priming site;

i) hybridizing the adaptor to the second and third primer extension products;

j) ligating one strand of the adaptor to the second and third primer extension products to form ligation products;

k) hybridizing a fourth target-specific primer to the second primer extension product and a fifth primer to the third primer extension product wherein the fourth and fifth target-specific primers comprise a target-binding site and a universal priming site; and l) amplifying the ligation products utilizing primers hybridizing to the universal priming sites.

The present invention also provides kit for simultaneously enriching for DNA and RNA targets from samples comprising: a first target-specific primer comprising a target-binding region and a region of complementarity to an adaptor, a reverse transcriptase, a second target-specific primer comprising a target-binding region and a region of complementarity to the adaptor, a DNA polymerase to form a second primer extension product; the adaptor comprising a longer strand and a shorter strand wherein the longer strand comprises a region complementary to the region in the first and second target-specific primers, and the shorter strand comprises a universal priming site; and optionally, universal primers and reagents for DNA ligation and DNA amplification. The kit may further comprise reagents for sequencing the enriched DNA and RNA targets.

The present invention also provides reaction mixture for simultaneously enriching for DNA and RNA targets from samples comprising: a first target-specific primer comprising a target-binding region and a region of complementarity to an adaptor, a reverse transcriptase, a second target-specific primer comprising a target-binding region and a region of complementarity to the adaptor, a DNA polymerase to form a second primer extension product; the adaptor comprising a longer strand and a shorter strand wherein the longer strand comprises a region complementary to the region in the first and second target-specific primers, and the shorter strand comprises a universal priming site.

BRIEF DESCRIPTION OF THE DRAWINGS

FIG. 7 is a detailed view highlighting the single-stranded overhang region of embodiments of the adaptor of FIG. 6.

DETAILED DESCRIPTION OF THE INVENTION

Definitions

Figure 1:
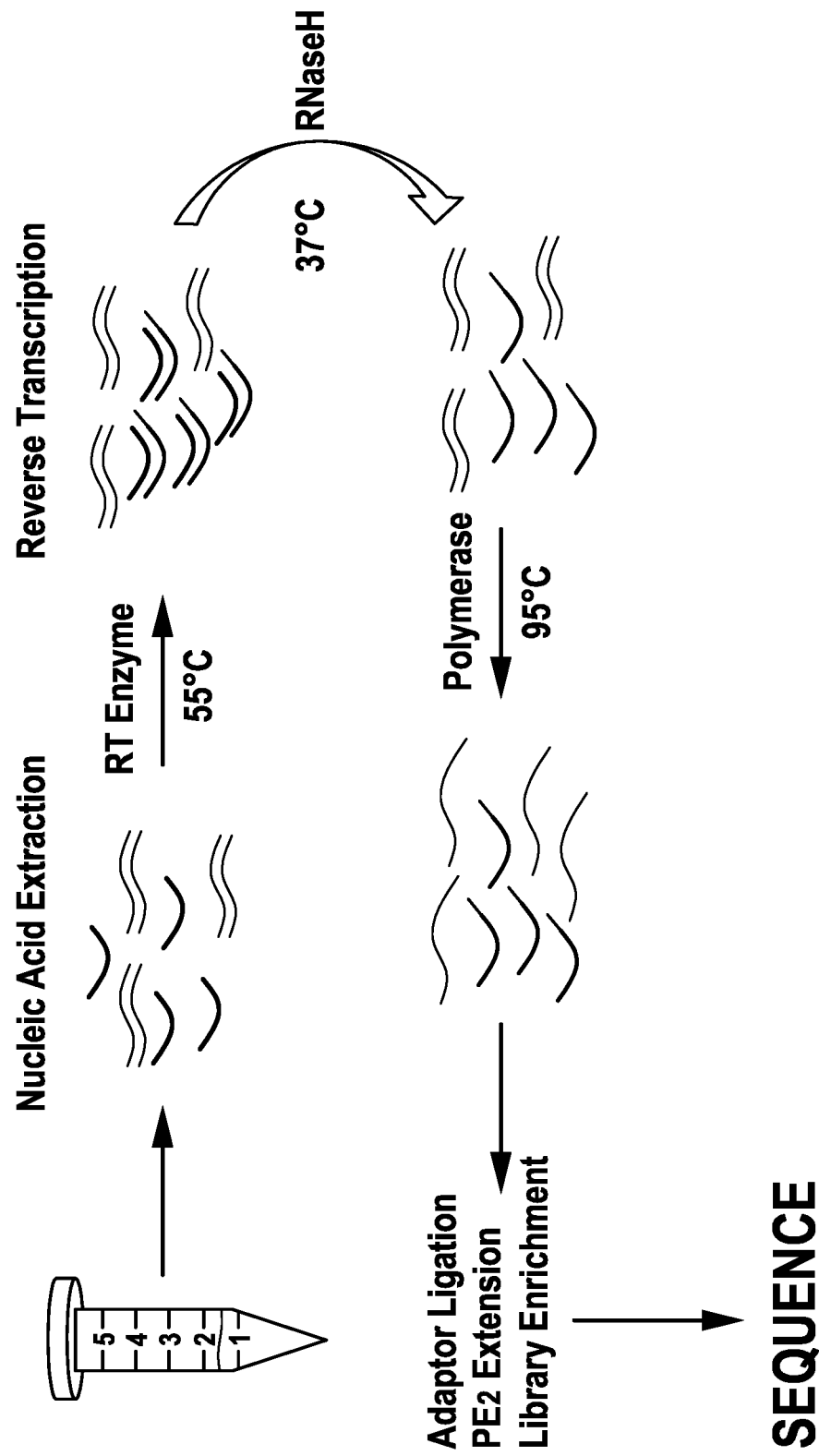
FIG. 1 is an overview diagram of the workflow of the invention.

Unless defined otherwise, technical and scientific terms used herein have the same meaning as commonly understood by a person of ordinary skill in the art. See, Sambrook et al., *Molecular Cloning, A Laboratory Manual*, 4$^{th}$ Ed. Cold Spring Harbor Lab Press (2012).

The following definitions are provided to facilitate understanding of the present disclosure.

The term "barcode" refers to a nucleic acid sequence that can be detected and identified. Barcodes can generally be 2 or more and up to about 50 nucleotides long. Barcodes are designed to have at least a minimum number of differences from other barcodes in a population. Barcodes can be unique to each molecule in a sample or unique to the sample and be shared by multiple molecules in the sample.

The term "multiplex identifier," "MID" or "sample barcode" refer to a barcode that identifies a sample or a source of the sample. As such, all or substantially all, MID barcoded polynucleotides from a single source or sample will share an MID of the same sequence; while all, or substantially all (e.g., at least 90% or 99%), MID barcoded polynucleotides from different sources or samples will have a different MID barcode sequence. Polynucleotides from different sources having different MIDs can be mixed and sequenced in parallel while maintaining the sample information encoded in the MID barcode.

The term "unique molecular identifier" or "UID," refer to a barcode that identifies a polynucleotide to which it is attached. Typically, all, or substantially all (e.g., at least 90% or 99%), UID barcodes in a mixture of UID barcoded polynucleotides are unique.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologues, SNPs, and complementary sequences as well as the sequence explicitly indicated.

The term "polymerase" refers to an enzyme that performs template-directed synthesis of polynucleotides. DNA polymerases include prokaryotic Pol I, Pol II, Pol III, Pol IV and Pol V, eukaryotic DNA polymerase, archaeal DNA polymerase, telomerase and reverse transcriptase. The term "thermostable polymerase," refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. In some embodiments, the following thermostable polymerases can be used: *Thermococcus litoralis* (Vent, GenBank: AAA72101), *Pyrococcus furiosus* (Pfu, GenBank: D12983, BAA02362), *Pyrococcus woesii*, *Pyrococcus* GB-D (Deep Vent, GenBank: AAA67131), *Thermococcus kodakaraensis* KODI (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: 029753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* sp. GE8 (GenBank: CAC12850), *Thermococcus* sp. JDF-3 (GenBank: AX135456; WO0132887), *Thermococcus* sp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* sp. GE23 (GenBank: CAA90887), *Pyrococcus* sp. ST700 (GenBank: CAC 12847), *Thermococcus pacificus* (GenBank: AX411312.1), *Thermococcus zilligii* (GenBank: DQ3366890), *Thermococcus aggregans*, *Thermococcus barossii*, *Thermococcus celer* (GenBank: DD259850.1), *Thermococcus profundus* (GenBank: E14137), *Thermococcus siculi* (GenBank: DD259857.1), *Thermococcus thioreducens*, *Thermococcus onnurineus* NA1, *Sulfolobus acidocaldarium*, *Sulfolobus tokodaii*, *Pyrobaculum calidifontis*, *Pyrobaculum islandicum* (GenBank: AAF27815), *Methanococcus jannaschii* (GenBank: Q58295), *Desulforococcus species* TOK, *Desulfurococcus*, *Pyrolobus*, *Pyrodictium*, *Staphylothermus*, *Vulcanisaetta*, *Methanococcus* (GenBank: P52025) and other archacal B polymerases, such as GenBank AAC62712, P956901, BAAA07579)), thermophilic bacteria *Thermus* species (e.g., *flavus, ruber, thermophilus, lacteus, rubens, aquaticus*), *Bacillus stearothermophilus*, *Thermotoga maritima*, *Methanothermus fervidus*, KOD polymerase, TNA1 polymerase, *Thermococcus* sp. 9 degrees N-7, T4, T7, phi29, *Pyrococcus furiosus, P. abyssi, T. gorgonarius, T. litoralis, T. zilligii, T.* sp. GT, *P.* sp. GB-D. KOD, Pfu, *T. gorgonarius, T. zilligii, T. litoralis* and *Thermococcus* sp. 9N-7 polymerases. In some cases, the nucleic acid (e.g., DNA or RNA) polymerase may be a modified naturally occurring Type A polymerase. A further embodiment of the invention generally relates to a method wherein a modified Type A polymerase, e.g., in a primer extension, end-modification (e.g., terminal transferase, degradation, or polishing), or amplification reaction, may be selected from any species of the genus *Meiothermus*, *Thermotoga*, or *Thermomicrobium*. Another embodiment of the invention generally pertains to a method wherein the polymerase, e.g., in a primer extension, end-modification (e.g., terminal transferase, degradation or polishing), or amplification reaction, may be isolated from any of *Thermus aquaticus* (Taq), *Thermus thermophilus*, *Thermus caldophilus*, or *Thermus filiformis*. A further embodiment of the invention generally encompasses a method wherein the modified Type A polymerase, e.g., in a primer extension, end-modification (e.g., terminal transferase, degradation, or polishing), or amplification reaction, may be isolated from *Bacillus stearothermophilus*, *Sphaerobacter thermophilus*, *Dictoglomus thermophilum*, or *Escherichia coli*. In I another embodiment, the invention generally relates to a method wherein the modified Type A polymerase, e.g., in a primer extension, end-modification (e.g., terminal transferase, degradation, or polishing), or amplification reaction, may be a mutant Taq-E507K polymerase. Another embodiment of the invention generally pertains to a method wherein a thermostable polymerase may be used to effect amplification of the target nucleic acid.

The term "primer" refers to an oligonucleotide which binds to a specific region of a single-stranded template nucleic acid molecule and initiates nucleic acid synthesis via a polymerase-mediated enzymatic reaction. Typically, a primer comprises fewer than about 100 nucleotides and preferably comprises fewer than about 30 nucleotides. A target-specific primer specifically hybridizes to a target polynucleotide under hybridization conditions. Such hybridization conditions can include, but are not limited to, hybridization in isothermal amplification buffer (20 mM Tris-HCl, 10 mM $(NH_4)_2SO_4$, 50 mM KCl, 2 mM $MgSO_4$, 0.1% TWEEN® 20, pH 8.8 at 25° C.) at a temperature of about 40° C. to about 70° C. In addition to the target-binding region, a primer may have additional regions, typically at 5'-portion. The additional region may include universal primer binding site or a barcode.

The term "universal primer" refers to a primer that can hybridize to a universal primer binding site. Universal primer binding sites can be natural or artificial sequences typically added to a target sequence in a non-target-specific manner.

The term "sample" refers to any biological sample that comprises nucleic acid molecules, typically comprising DNA or RNA. Samples may be tissues, cells or extracts thereof, or may be purified samples of nucleic acid molecules. Use of the term "sample" does not necessarily imply the presence of target sequence among nucleic acid molecules present in the sample.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

Nucleic acid sequencing is rapidly expanding into clinical practice. The current sequencing technologies employ single molecule sequencing and allow detection of extremely rare targets. Among the clinical applications of nucleic acid sequencing is "liquid biopsy" e.g., detection and monitoring of malignant tumors using a blood sample instead of a traditional invasive biopsy. Tumor DNA is distinguished by the presence of mutations, including single nucleotide variations or small sequence variations as well as gene fusions. See Newman, A., et al., (2014) An ultrasensitive method for quantitating circulating tumor DNA with broad patient coverage, Nature Medicine doi: 10.1038/nm.3519 and F. Mertens, et al. (2015) The emerging complexity of gene fusions in cancer, Nat. Rev. Cancer 15:371

These and other challenges may be overcome with a method for target enrichment by single probe primer extension according to the present disclosure. In one aspect, the present disclosure describes both a general approach for single probe primer extension based enrichment as well as improvements therefor. The improvements described herein include, but are not limited to, alternative purification methods, workflow modifications (e.g., alternative enzymes, reductions in the number of overall steps, improved thermal cycling profiles), alternative adaptor designs, and changes to enable to the application of the disclosed methods to both simultaneous enrichment of RNA and DNA, and digital droplet PCR.

In one embodiment, the invention is a method of amplifying a target sequence comprising the steps of: contacting the target nucleic acid with a primer and a polymerase, wherein the primer comprises a target-binding site and a unique molecular identification tag (UID); conducting a polymerase extension reaction and a termination to create a single-stranded primer extension product; ligating adaptors to each end of the single-stranded primer extension product to create a ligation product, wherein adaptors comprise at least one universal priming site; amplifying the ligation product in an amplification reaction utilizing at least one primer binding to the at least one universal priming site to create the amplified target sequence. In some embodiments, the primer and at least one of the adaptors comprise mutually compatible universal ligation sites. In some embodiments, the target-binding site is a pre-designed target-specific sequence. In some embodiments, the target-binding site is a random sequence. In some embodiments, the termination is effected by a method selected from the list consisting of temperature shift, addition of a specific enzyme inhibitor, addition of a chelator, incorporation of uridine-containing bases followed by treatment with uracil-N-DNA glycosylase. In some embodiments, at least one adaptor comprises a barcode. The barcode can be a multiplex sample ID (MID). The amplification can be linear amplification or exponential amplification. In some embodiments, the method further comprises a purification step after at least one of primer extension and ligation.

In other embodiments, the invention is a kit for amplifying a target sequence comprising: a primer comprising a target-binding site, a unique molecular identification tag (UID), and a universal ligation site; at least one adaptor comprising at least one universal priming site, multiplex sample ID (MID) and a universal ligation site. In some embodiments, the kit comprises two adaptors having different universal priming sites but only one adaptor comprising the universal ligation site and the MID. In some embodiments, the kit further comprises one or more of the following: nucleic acid polymerase, ligase, thermostable DNA polymerase, and universal primers.

Detecting individual molecules typically requires molecular barcodes such as described in U.S. Pat. Nos. 7,393,665, 8,168,385, 8,481,292, 8,685,678, and 8,722,368. A unique molecular barcode is a short artificial sequence added to each molecule in the patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy (Newman, A., et al., (2014) An ultrasensitive method for quantitating circulating tumor DNA with broad patient coverage, Nature Medicine doi: 10.1038/nm.3519).

Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample (Newman, A., et al., (2016) Integrated digital error suppression for improved detection of circulating tumor DNA, Nature Biotechnology 34:547).

In some embodiments, the invention is a library of barcoded nucleic acid molecules for sequencing. In some embodiments, the invention is a method of sequencing nucleic acids via creation of a barcoded library of nucleic acid molecules.

The present invention comprises detecting a target nucleic acid in a sample by nucleic acid sequencing. Multiple nucleic acids, including all the nucleic acids in a sample may be detected using the method and compositions described herein. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, or fecal samples). The sample may comprise whole blood or blood fractions where normal or tumor cells may be present. In some embodiments, the sample, especially a liquid sample may comprise cell-free material such as cell-free DNA or RNA including cell-free tumor DNA or tumor RNA. In some embodiments, the sample is a cell-free sample, e.g., cell-free blood-derived sample where cell-free tumor DNA or tumor RNA are present. In other embodiments, the sample is a cultured sample, e.g., a culture or culture supernatant containing or suspected to contain nucleic acids derived from the cells in the culture or from an infectious agent present in the culture. In some embodiments, the infectious agent is a bacterium, a protozoan, a virus or a mycoplasma.

A target nucleic acid is the nucleic acid of interest that may be present in the sample. In some embodiments, the target nucleic acid is a gene or a gene fragment, or a transcript or a portion of the transcript to which target-specific primers hybridize. In some embodiments, multiple genes, gene fragments, intergenic regions and gene transcripts constitute target nucleic acids. In some embodiments, the target nucleic acid contains a locus of a genetic variant, e.g., a polymorphism, including a single nucleotide polymorphism or variant (SNP of SNV), or a genetic rearrangement resulting e.g., in a gene fusion. In some embodiments, the target nucleic acid comprises a biomarker, i.e., a gene whose variants are associated with a disease or condition. In other embodiments, the target nucleic acid is characteristic of a particular organism and aids in identification of the organism or a characteristic of the pathogenic organism such as drug sensitivity or drug resistance. In yet other embodiments, the target nucleic acid is a unique characteristic of a human subject, e.g., a combination of HLA or KIR sequences defining the subject's unique HLA or KIR genotype.

In some embodiments, the target nucleic acid occurs in nature in a single-stranded form (e.g., RNA, including mRNA, microRNA, viral RNA; or single-stranded viral DNA). In other embodiments, the target nucleic acid occurs in nature in a double-stranded form. One of skill in the art would recognize that the method of the invention is capable of simultaneously enriching for the target nucleic acid in both RNA and DNA forms and is effective whether one or both forms are present in the sample. Longer target nucleic acids may be fragmented. In some embodiments, the target nucleic acid is naturally fragmented, e.g., circulating cell-free DNA (cfDNA) or chemically degraded DNA such as the one founds in preserved samples.

The present invention comprises the use of one adaptor molecule to be ligated to the end of a primer extension product. In some embodiments, the partially single-stranded adaptor is hybridized to the single-stranded primer extension product to create a partially double-stranded molecule with a nick in one strand. Ligation of the strand with a nick is well known in the art (See Green M., and Sambrook, J., *Molecular Cloning,* 2012 CSHL Press).

In some embodiments, the adaptor molecules are in vitro synthesized artificial sequences. In other embodiments, the adaptor molecules are in vitro synthesized naturally-occurring sequences. In yet other embodiments, the adaptor molecules are isolated naturally occurring molecules or isolated non naturally-occurring molecules.

In some embodiments, the adaptor comprises one or more barcodes. A barcode can be a multiplex sample ID (MID) used to identify the source of the sample where samples are mixed (multiplexed). The barcode may also serve as a unique molecular ID (UID) used to identify each original molecule and its progeny. The barcode may also be a combination of a UID and an MID. In some embodiments, a single barcode is used as both UID and MID. In some embodiments, each barcode comprises a predefined sequence. In other embodiments, the barcode comprises a random sequence.

In some embodiments, the amplified molecules generated by the method of the present invention comprise at least one and in some embodiments, at least two barcodes. At least one barcode is a UID and at least two barcodes comprise a UID and an MID. In some embodiments of the invention, the barcodes are between about 4-20 bases long so that between 96 and 384 different adaptors, each with a different pair of identical barcodes are added to a human genomic sample. A person of ordinary skill would recognize that the number of barcodes depends on the complexity of the sample (i.e., expected number of unique target molecules) and would be able to create a suitable number of barcodes for each experiment.

In some embodiments, the invention utilizes target-specific primers. A target specific primer comprises at least a portion that is complementary to the target. If additional sequences are present, they are typically in 5'-portion of the primer. In some embodiments, the same primer or a pair of target-specific primers can be used for the RNA and DNA version of the target. In other embodiments, only one target-specific primer is shared and the second target-specific primer is different. In yet other embodiments, the target-specific primers are specific for different genes, e.g., the second target specific primer is specific for a gene fusion partner. In yet other embodiments, the primers used for DNA target different genes or loci than the primers used for RNA targets.

The adaptor further comprises a primer binding site for at least one universal primer. One of skill in the art will recognize that a double stranded adaptor sequence will have a primer binding site on one strand and a sequence identical to the primer on the other strand. One of ordinary skill would also recognize that a single stranded primer (e.g., a target-specific primer) will have a 5'-sequence identical to the primer that will be copied into a primer binding site in the complementary strand.

In some embodiments, the invention comprises an amplification step. This step can involve linear or exponential amplification, e.g., PCR. Amplification may be isothermal or involve thermocycling. In some embodiments, the amplification is exponential and involves PCR. Universal primers are used, i.e., a single pair of primers hybridizes to a binding site in the adaptor present on all target sequences in the sample. All molecules in the library having the same adaptor can be amplified with the same set of primers. Because PCR with universal primers has reduced sequence bias, the number of amplification cycles need not be limited. The number of amplification cycles where universal primers are used can be low but also can be 10, 20 or as high as about 30 or more cycles, depending on the amount of product needed for the subsequent steps.

The amplicons generated from the target nucleic acids can be subjected to nucleic acid sequencing. Sequencing can be performed by any method known in the art. Especially advantageous is the high-throughput single molecule sequencing. Examples of such technologies include the Illumina HiSeq platform (Illumina, San Diego, Cal.), Ion Torrent platform (Life Technologies, Grand Island, NY), Pacific BioSciences platform utilizing the SMRT (Pacific Biosciences, Menlo Park, Cal.) or a platform utilizing nanopore technology such as those manufactured by Oxford Nanopore Technologies (Oxford, UK) or Roche Sequencing Solutions (Santa Clara, Cal.) and any other presently existing or future DNA sequencing technology that does or does not involve sequencing by synthesis. The sequencing step may utilize platform-specific sequencing primers. Binding sites for these primers may be introduced in 5'-portions of the amplification primers used in the amplification step. If no primer sites are present in the library of barcoded molecules, an additional short amplification step introducing such binding sites may be performed.

In some embodiments, the sequencing step involves sequence analysis. In some embodiments, the analysis includes a step of sequence aligning. In some embodiments, aligning is used to determine a consensus sequence from a plurality of sequences, e.g., a plurality having the same barcodes (UID). In some embodiments barcodes (UIDs) are used to determine a consensus from a plurality of sequences all having an identical barcode (UID). In other embodiments, barcodes (UIDs) are used to eliminate artifacts, i.e., variations existing in some but not all sequences having an identical barcode (UID). Such artifacts resulting from PCR errors or sequencing errors can be eliminated.

In some embodiments, the number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

Simultaneous analysis of RNA and DNA material from the same sample has substantial utility in the clinic. For many types of samples the amount and quality of nucleic acids is limited making detection of a particular target difficult. The use of both DNA and RNA maximizes the amount of available targets while also taking advantage of the unique property of each type of nucleic acid. For example, DNA holds the information about mutations, including single nucleotide variants (SNVs) and copy number variations (CNVs). In addition, the information derived from the DNA can be quantitative, i.e., reflect not only the type of mutation but also the mutation burden in the tumor sample. By contrast, RNA provides qualitative information about mutations as the varying expression levels obscure the mutation burden in the genome. At the same time, gene transcription amplifies the signal from a rare mutation event making it easier to detect. Analysis of RNA is especially useful for detecting gene fusions in the background of wild-type DNA sequences from both fusion partners.

In some embodiments, the invention comprises a method of primer extension target enrichment (PETE) applied exclusively to RNA. Described generally, the method comprises reverse transcription of RNA molecules followed by primer extension target enrichment. Examples of primer extension target enrichment have been previously described by the present inventors in U.S. Provisional Application Ser. No. 62/344,330, filed on Jun. 1, 2016, Ser. No. 62/361,426 filed on Jul. 12, 2016 and U.S. application Ser. No. 15/228,806 filed on Aug. 4, 2016.

In some embodiments, the invention comprises a method of primer extension target enrichment applied to an unseparated mixture of RNA and DNA. In some embodiments, the mixture comprises total RNA and genomic DNA, i.e., nucleic acids isolated from the sample with minimum processing. Described generally, the method comprises reverse transcription of RNA molecules while DNA molecules are passively present, followed by primer extension target enrichment applied to both genomic DNA molecules and cDNA molecules.

In some embodiments, the invention comprises intermediate purification steps. In some embodiments, the unused single DNA and RNA strands are removed with exonuclease. In some embodiments, the unused primers and adaptors are removed, e.g., by a size selection method selected from gel electrophoresis, affinity chromatography and size exclusion chromatography. In some embodiments, size selection can be performed using Solid Phase Reversible Immobilization (SPRI) technology from Beckman Coulter (Brea, Cal.).

In some embodiments, the DNA polymerase is a thermostable polymerase. In some embodiments, the same polymerase performing the primer extension step can be used in PCR amplification. In some embodiments, the DNA polymerase possesses a hot-start capability. The hot-start capability comprises inhibition of the polymerase at ambient temperatures via a mechanism selected from antibody interaction, chemical modification or aptamers interaction.

Figure 2:
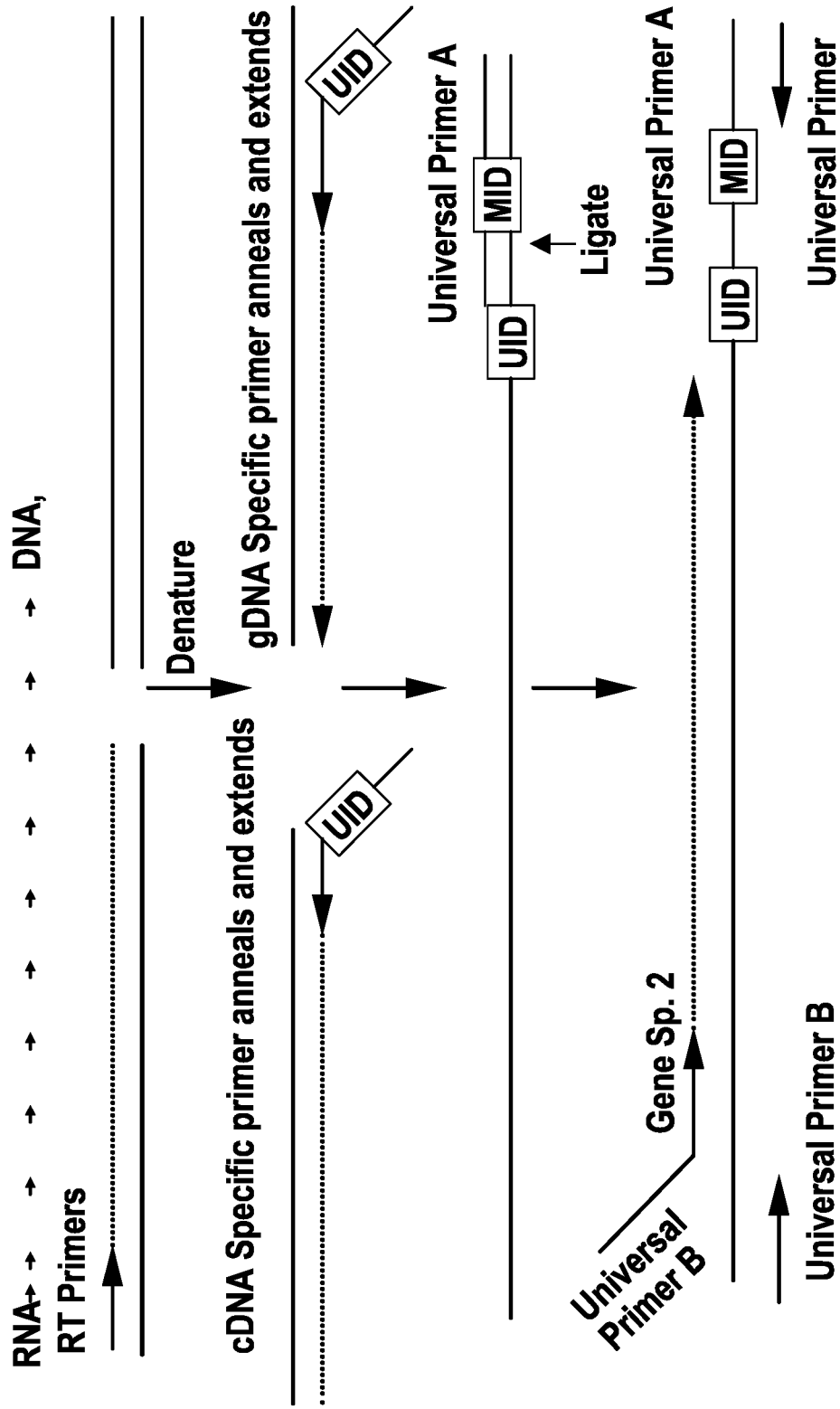
FIG. 2 is a diagram of the workflow of the invention including the simultaneous enrichment of DNA and RNA.

The invention is represented in more detail in FIGS. 1-2. FIG. 1 depicts an exemplary workflow of the invention. Total nucleic acids are isolated from the sample. In the first step, RNA is subjected to reverse transcription while the DNA remains double-stranded. After RNA is removed with RNase H, only the cDNA strands remain. Following denaturation, primer extension can take place on DNA targets. Next, both DNA-derived and RNA-derived primer extension products are subjected to the Primer Extension Target Enrichment (PETE) procedure and sequencing.

FIG. 2 depicts an exemplary workflow of the invention with PETE steps shown in detail. First, a reverse transcription step generates cDNA from an RNA strand. Next, target-specific primers with UID anneal to both cDNA strands and denatured genomic DNA strands. A partially single-stranded adaptor has an MID, a universal primer site and a sequence than can anneal to 5'-portion of the target-specific primers present in the sample. One strand of the resulting complex contains a nick that can be sealed with a ligase. A second target-specific primer is used to introduce a second universal primer site. The primer extension product can be amplified with universal primers.

Figure 4:
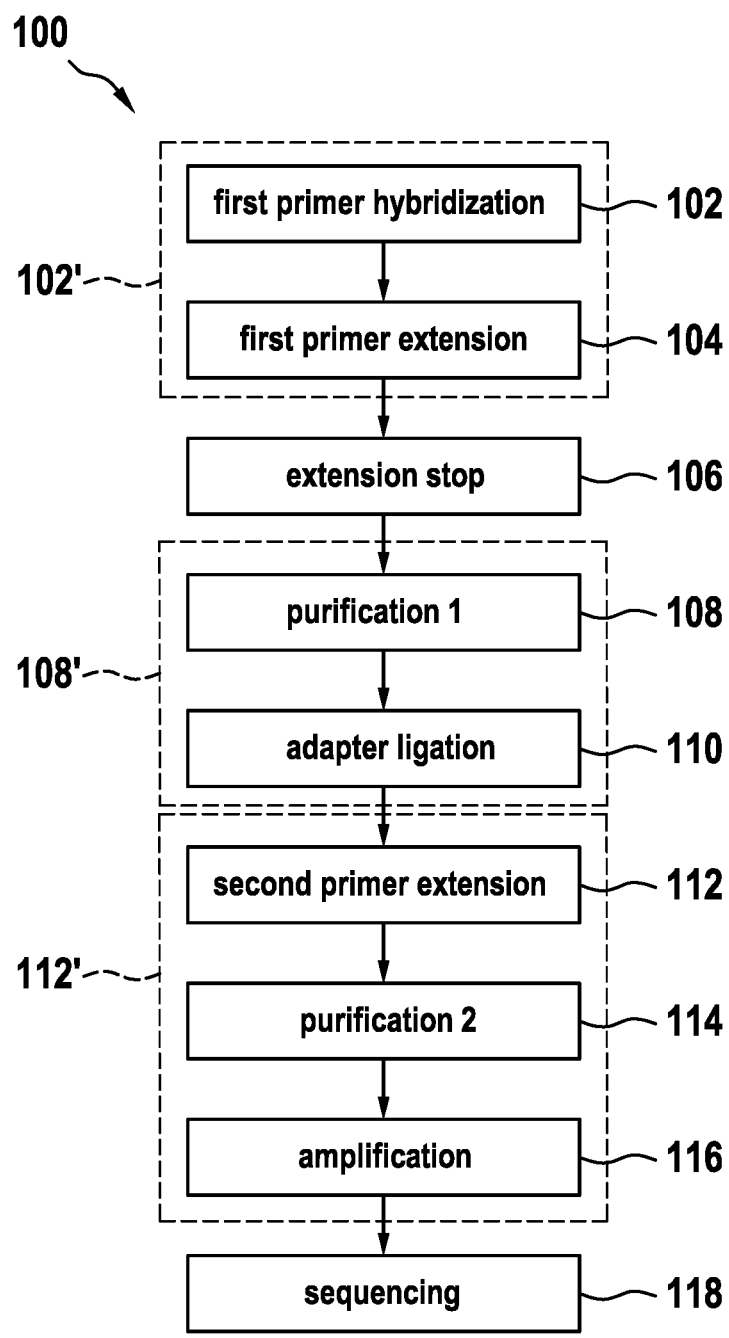
FIG. 4 is a schematic flow diagram illustrating the method of FIG. 2.

Turning now to FIG. 4, a method 100 for target enrichment by single probe primer extension includes a step 102 of primer hybridization in which a first primer is hybridized to a nucleic acid present in a sample. In one aspect, the first primer is a target specific primer. One example of a target specific primer is a gene specific primer designed to hybridize to or nearby (e.g., upstream of, or 5' to) a gene (e.g., cDNA, genomic DNA) of interest. The nucleic acid in the sample can be RNA, DNA, or a combination thereof. The primer can be an oligonucleotide primer composed of ribonucleic acids, deoxyribonucleic acids, modified nucleic acids (e.g., biotinylated, locked nucleic acids, inosines, Seela bases, or the like), or other nucleic acid analogs known in the art.

With continued reference to FIG. 4, the step 102 is followed by a step 104 of primer extension by a polymerase. In one aspect, following hybridization of the first primer to the nucleic acid template, the first primer is extended by the polymerase, thereby generating a first primer extension product including a 3' region comprising the reverse complement of the nucleic acid template. As described herein, the step 102 and the step 104 are optionally performed simultaneously, whereas in other embodiments, the step 102 and the step 104 are performed separately (e.g., sequentially). Accordingly, in some embodiments of the disclosed method, the step 102 and the step 104 are combined into a single step 102'.

The method 100 further includes a step 106 of extension stop in order to control the length of the first primer extension product synthesized in the step 104 (or the step 102'). Notably, the length of the first primer extension product can be controlled actively through techniques such as inactivating the polymerase added in the step 104, or passively by enabling the reaction to go to completion such as through the consumption of limiting reactants or by fragmenting the nucleic acid template prior to performing the steps of the method 100.

In one aspect, the method 100 can further include one or more purification steps. In the illustrated embodiment, the method 100 includes a first purification step 108 (i.e., purification 1) following the first primer extension step 104 and the extension stop step 106. The step 108 can include any suitable method for the purification of the first primer extension product from reaction components such as unused primer molecules, template nucleic acid molecules used to create the primer extension product, or the like. In some embodiments, the step 108 includes enzymatic digestion, size-exclusion based purification, affinity-based purification, the like, or a combination thereof.

The method 100 further includes a step 110 of adaptor ligation. Adaptors can have any suitable composition including, but not limited to, a homopolymer tail, a universal priming site, a sample identifier or molecular identifier (MID), a unique identifier (UID) or barcode, the like, and combinations thereof. As described herein, the exact mode of ligating the adaptor is immaterial as long as the adaptor becomes associated with the primer extension product and enables subsequent steps described below. In one aspect, the adaptors with universal priming sites may be added by any single-stranded ligation methods available in the art to one or both ends of the first primer extension product.

Figure 5:
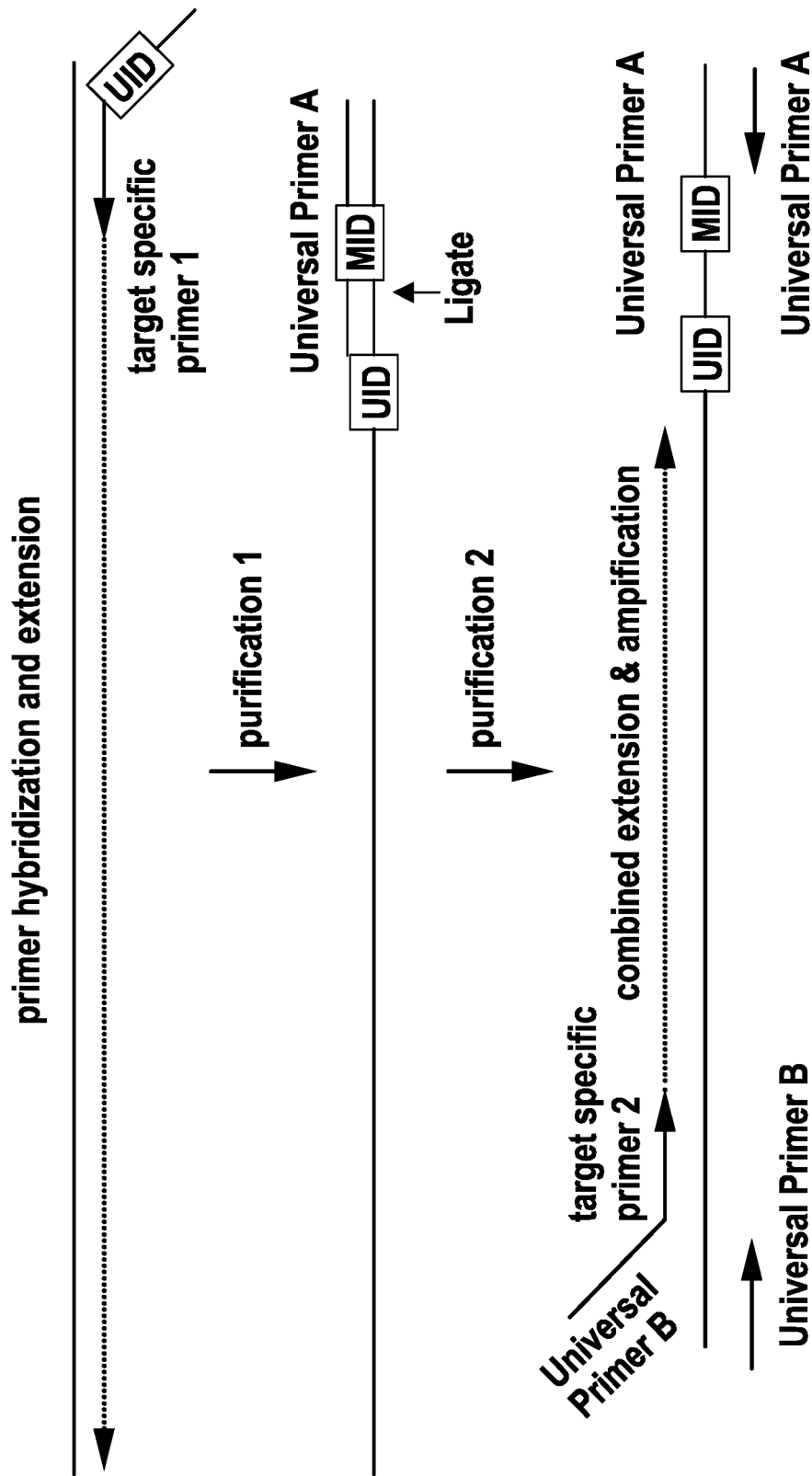
FIG. 5 is a schematic representation of an embodiment of a method according to the present disclosure in which the second primer extension step and the universal primer amplification step are combined into a single step.

The method 100 can further include an optional second primer extension step 112. For example, a ligated adaptor having a free 3'-end can be extended by a polymerase towards 5' end of the first primer extension product to create a double-stranded nucleic acid product. A second target specific primer in the opposing direction relative to the first target-specific primer can also be used (FIG. 5). Thereafter, the method 100 can include a second purification step 114 (i.e., purification 2) following the adaptor ligation step 110 and optionally the second primer extension step 112. The second purification step 114 can be useful for the removal of reaction components such as unused adaptor molecules or the like. Accordingly, unligated adaptors and by-products of the step 110 are separated from the adaptor-ligated first (or second) extension products by any suitable purification method.

The method 100 further includes a step 116 of amplification. The step 116 can involve linear or exponential amplification (e.g., PCR). In general, the step 116 includes amplification of the first (or second) adaptor-ligated primer extension product. In some embodiments, he primers are universal primers that can support synthesis of one or both strands into which universal primer binding sites have been introduced. (i.e., both the top and bottom strands of a double-stranded nucleic acids corresponding to the template of the amplification reaction).

After the step 116 of amplification, the method 100 can include a step 118 of sequencing. The step 116 can include any method for determining the nucleic acid sequence of one or more products of the method 100. The step 116 can further include sequences alignment, identification of sequence variations, counting of unique primer extension products, the like, or combinations thereof. In some embodiments, an additional purification step is performed prior to sequencing 118.

EXAMPLES

Example 1. Detection of Known Fusion Targets

In this example, the sensitivity of the assay was assessed using 3 cell lines known to express 5 clinically relevant fusion genes. A set of primers (probes) targeting an RNA fusion panel including 24 ALK, 11 RET and 15 ROS1 was designed (Table 1).

TABLE 1

| Fusions in the panel | | |
|---|---|---|
| ALK FUSIONS (24) | RET FUSIONS (8) | ROS FUSIONS (15) |
| EML4 E13; ALK E20 Variant 1 | KIF5B E22; RET E12 | CD74 E6; ROS1 E32 |
| EML4 E20; ALK A20 Variant 2 | KIF5B E23; RET E12 | CD74 E6; ROS1 E34 |
| EML4 E6a; ALK A20 Variant 3a | KIF5B E24; RET R11 | SDC4 E2; ROS1 E32 |
| EML4 E6b; ALK A20 Variant 3b | KIF5B E24; -RET E8 | SDC4 E4; ROS1 E32 |
| EML4 E14; ins11del49ALK A20 Variant 4 | CCDC6 E1; RET E12 | SDC4 E4; ROS1 E34 |
| EML4 E2; ALK A20 Variant 5a | NCOA4 E6; RET E12 | SLC34A2 E13; ROS E32 |
| EML4 E2; ins117ALK A20 Variant 5b | TRIM33 E14; RET E12 | SLC34A2 E13; ROS1 E33 |
| EML4 E13; ins69ALK A20 Variant 6 | TRIM33 E11; RET E12 | SLC34A2 E13; ROS1 E34 |
| EML4 E14; del12, 114, 136ALK A20 Var. 7 | | SLC34A2 E4; ROS1 E32 |
| EML4 E15del19; del20ALK A20 "V4" | | SLC34A2 E4; ROS1 E34 |
| EML4 E18; ALK A20 "V5" | | EZR E10; ROS1 E34 |
| EML4 E17; ALK A20 Variant 8 | | LRIG3 E16; ROS1 E35 |
| EML4 E17; ins30ALK A20 Variant 8a | | GOPC E7; ROS1 R35 |
| EML4 E17ins61; ins34ALK A20 Var. 8b-1 | | TPM3 E8; ROS1 E35 |
| EML4 E17del58ins39; ALK A20 Var. 8b-2 | | CLTC E31; ROS1 E35 |
| EML4 E17ins65; ALK A20 Variant 8b-3 | | |
| EML4 E17ins68; ALK A20 Variant 8b-4 | | |
| EML4 E6; ALK A19 | | |
| KIF5B E24; ALK E20 | | |
| KIF5B E17; ALK E20 | | |
| KIF5B E15; ALK E20 | | |
| HIP1; ALK | | |
| KLC1 E9; ALK E20 | | |
| TFG; ALK | | |

The panel covers a total of 61 targets (49 fusions, 10 wild type genes and 2 housekeeping genes) using 10 probes for reverse transcription and 42 probes for the second extension step. The libraries created using the RNA PETE workflow (FIGS. 1 and 2) were sequenced on an Illumina MiSeq instrument. All of the 5 fusions reported to be present in the original cell lines were detected. The deduped depth of each fusion oncogene (calculated based on the unique molecular ID counts) was in correlation with their expression levels in the cell lines.

In this experiment, the reverse transcription step, the sample nucleic acids were mixed with primers and incubated at 40° C. The reaction further included dNTPs, DTT, RNase inhibitor and SuperScript® III reverse transcriptase (ThermoFisher Scientific, Waltham, Mass.) according to the manufacturer's instructions. The primer extension products in the sample were purified using AMPure beads (Beckman Coulter, Brea, Cal.). Adaptor was ligated using T7 ligase at 25° C. for 5 minutes. The ligation products in the sample were purified using AMPure beads. The DNA primer extension was performed using Phusion® DNA polymerase (ThermoFisher Scientific) in the presence of ammonium sulfate according to the manufacturer's instructions. The extension was performed for 15 cycles in a thermocycler. The primer extension products in the sample were purified using AMPure beads.

Figure 3:
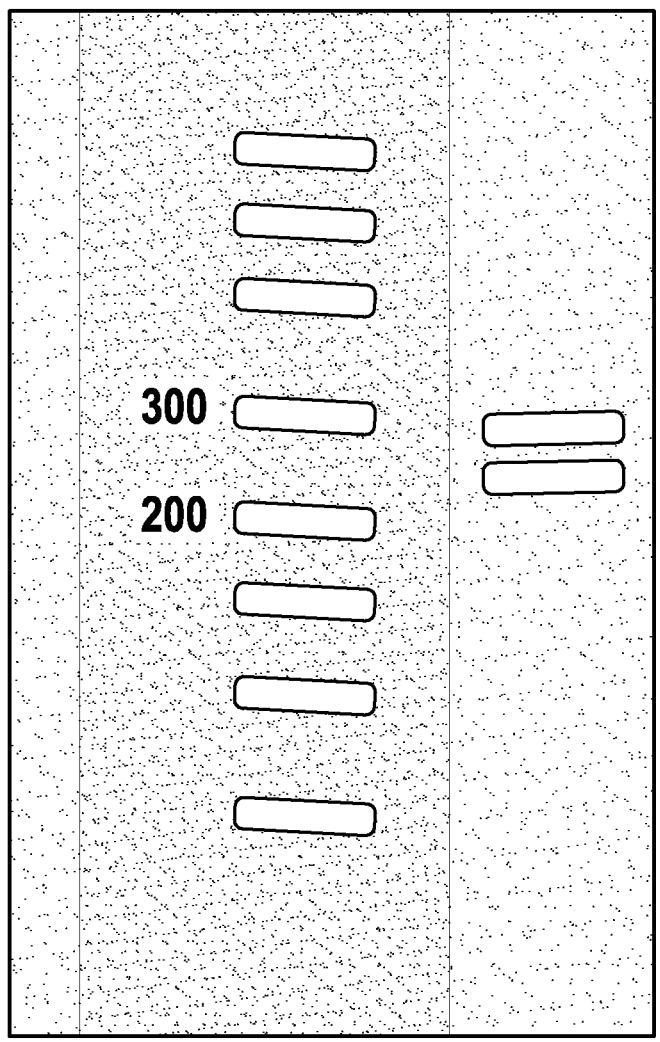
FIG. 3 illustrates the results of applying the method to an RNA target.

The final PETE products were amplified via 28 cycles of PCR with universal primers using Phusion® DNA polymerase. The amplification products were purified using AMPure beads. Results of the successful RNA PETE are shown on FIG. 3.

Example 2: Substitution of Exonuclease I for SPRI Bead Clean-Up

Exonuclease I is an enzyme that catalyzes the removal of nucleotides from single-stranded DNA in 3' to 5' direction. In the context of the present disclosure, an exonuclease I treatment step can be included as a purification step to degrade excess single-stranded primer oligonucleotides in preparation for downstream workflows. In one aspect, exonuclease I treatment is used in addition to or instead of an alternative purification step (e.g., step 108 of FIG. 4). Examples of alternative purification methods can include Solid Phase Reversible Immobilization (SPRI) bead-based purification methods, column-based clean-up methods, ethanol precipitation methods, or the like. The use of exonuclease I for the removal of excess primer oligonucleotides following the first primer extension step (e.g., step 104 of FIG. 4) and prior to the adaptor ligation step (e.g., step 110 of FIG. 4) has been demonstrated to exhibit similar results as compared to SPRI bead purification for the removal of excess primer oligonucleotides. Moreover, the use of exonuclease I can simplify the methods of the present disclosure by reducing the overall amount of hands-on time as compared with a workflow that relies on a SPRI bead purification step.

Example 3: Combination of PE2 and Universal Primer Amplification in a Single Reaction Step In some embodiments, a method according to the present disclosure includes a second target specific primer extension step followed sequentially by a universal primer amplification step. As illustrated in FIGS. 4 and 5, following the adaptor ligation step 110, and associated reaction purification steps, a method can include the second primer extension step 112 with a target specific primer and the amplification step 116 with a universal primer. The second primer extension step 112 and the amplification step 116 can be combined into a single step 112' (e.g., the two steps can be performed in a single reaction vessel without the need for intermediate clean-up steps, distinct reaction conditions and the like, or a combination thereof). In the case that the combined method step 112' is implemented, the second purification step 114 can be omitted as an intermediate step between the step 112 and the step 114 of the method 100. FIG. 5 further illustrates schematically the steps of an embodiment of the method 100 of FIG. 3 including the combined step 112'. Using the combined approach illustrated in FIGS. 4 and 5, it was demonstrated that the reverse target specific primers can be combined with universal primers with results comparable to a method including sequential primer extension and amplification steps. One advantage of a combined step of primer extension and universal amplification is a reduction in the overall workflow time in addition to a simplified workflow due to the reduced number of total steps. An example of a thermal cycling profile for a combined step of primer extension and universal amplification is shown in Table 2.

TABLE 2

Thermocycling profile for combined amplification and primer extension

| Step | Description | Temp. (° C.) | Time (sec) |
| --- | --- | --- | --- |
| 1 | Initial denaturation | 98 | 60 |
| 2 | Denaturation | 98 | 10 |
| 3 | Intermediate Temp | 80 | 0 |
| 4 | Annealing | 64 | 30 |
| 5 | Extension | 72 | 30 |
| | Repeat steps 2-5 (5x cycles) | | |
| 6 | Denaturation | 98 | 10 |
| 7 | Annealing | 68 | 30 |
| 8 | Extension | 72 | 30 |
| | Repeat steps 6-8 (25x cycles) | | |
| 9 | End | 4 | Hold |

Example 4: Use of Thermostable Polymerase with "Hot Start" Capability

According to the present disclosure, a thermally labile polymerase (e.g., Bst polymerase) is used in a first primer extension step (e.g., the step 104 of FIG. 4). When using a thermally labile polymerase, it can be useful to add the polymerase to the reaction mixture during the primer hybridization step (e.g., the step 102 of FIG. 4) following denaturation. In other embodiments, a thermally stable polymerase is used in place of a thermally labile polymerase. Use of a thermally stable polymerase has been demonstrated to enable the addition of the polymerase to the amplification or extension reaction mixture prior to the denaturation of a given target nucleic acid duplex.

Example 5: Adaptor Modifications

Figure 6:
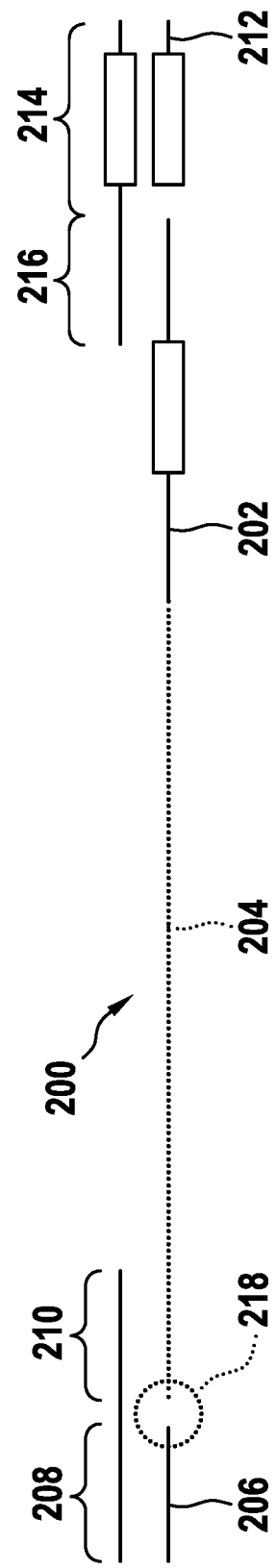
FIG. 6 is a schematic illustration of the adaptor ligated to the primer extension product.

As described herein, an adaptor can include a double-stranded region and a single stranded overhang complementary to a ligation site as shown in FIG. 2 and in more detail, in FIG. 6 and FIG. 7. The composition includes a primer extension product 200 having a 5' target specific primer region 202 and a 3' extended region 204. The composition further includes a first adaptor 206 having a double-stranded region 208 and a single-stranded 3'-overhang 210, and a second adaptor 212 having a double-stranded region 214 and a single-stranded 5'-overhang 216. Annealing of the single stranded 5'-overhang 216 of the second adaptor 212 to the 5' end of the target specific primer region 202 results in a gap 218 between the double-stranded region 214 of the second adaptor 212 and 5' end of the primer region 202. When the gap 218 is a nick (i.e., there is a zero nucleotide spacing between 5' end of the primer region 202 and the adjacent 3' end of the double-stranded region 214), the two strands can be ligated at the gap 218 by a DNA ligase or another enzyme, or a non-enzymatic reagent that can catalyze a reaction between the 3'-OH of the primer region 202 and 5'-phosphate of the second adaptor 212. The first adaptor 206 can be similarly annealed and ligated (e.g., through nick repair) to the 3' end of the extended region 204.

According to the present disclosure, the discovery has been made that decreasing the overall length in nucleotides of the double-stranded portion of the adaptor can reduce the formation of unwanted byproducts (e.g., primer dimers) in downstream amplification reactions. As further illustrated in FIG. 7, a generic adaptor 212a includes a double-stranded region 214a and a single-stranded 5'-overhang 216a that is designed to anneal to 5' end of the primer region 202. The double-stranded region 214a has an overall length in nucleotides of $[N]_i$, where N is an adaptor nucleotide and i is an integer representing the number of nucleotides in the double-stranded region 214a. A similar design is used for the adaptor 206 with a single stranded region 210 and double stranded region 208.

With continued reference to FIG. 7, an adaptor 212b having a double-stranded region 214b and a single-stranded 5'-overhang 216b illustrates an embodiment of the adaptor 212a where N=10. An adaptor 212c having a double-stranded region 214c and a single-stranded 5'-overhang 216c illustrates an embodiment of the adaptor 206a where N=15. According to the present disclosure, the adaptor 212b would, in general, be preferentially selected over the adaptor 212c for use in the methods described herein. In one aspect, an adaptor for ligation to a primer extension product has a double-stranded region of less than 10, less than 9, less than 8, less than 7, less than 6, less than 5, less than 4, less than 3, less than 2, or less than 1 nucleotide. Similar considerations are used for the adaptor 206 with a single stranded region 210 and double stranded region 208.

In another aspect, the discovery has been made that blocking 3'-end of an adaptor with a phosphate group (or another like blocking group) can reduce the formation of unwanted byproducts (e.g., primer dimers) in downstream amplification reactions. Moreover, it was demonstrated that an exonuclease I purification step and a ligation reaction step could be combined into a single reaction step in the case that a 3' phosphate block was included in the design of the single-stranded overhang of the adaptor. For example, the step 108, including an exonuclease I treatment, and the step 110 of the method 100 in FIG. 4 could be combined into a single step 108'. In yet another aspect, it was demonstrated that heat inactivation of exonuclease I was not required if the exonuclease treatment was performed prior to adaptor ligation. For example, in the case of the method 100 in FIG. 4, it may be useful to omit the heat inactivation of exonuclease I in between the purification step 108 and the adaptor ligation step 110.

Example 6: Subcycling

Figure 8:
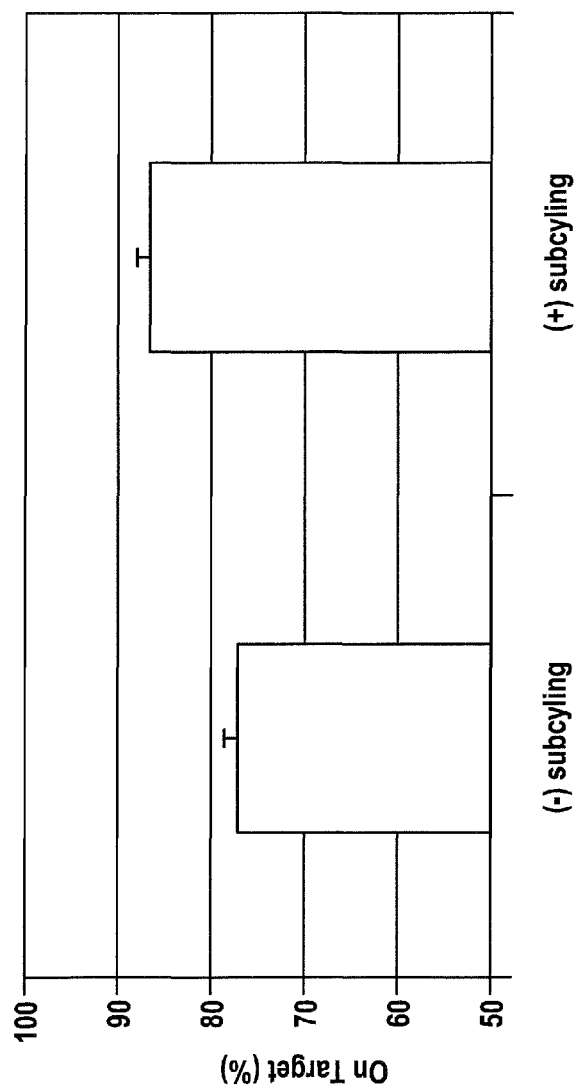
FIG. 8 is a bar graph illustrating the impact of subcyling on percent on-target when applied to a first primer extension reaction of a method according to the present disclosure.

Subcycling is a modified method of thermal cycling for PCR involving a combination of series of cycles with differing annealing temperatures. In one aspect, subcycling can be used to limit biases towards the amplification of one target sequence over another target sequence during multiplex PCR method (e.g., see Guido N. et al., 2016. *PLoS ONE* 11 (6): e0156478; Liu Q. et al., 1998. *Biotechniques* 25 (6): 1022-8). When implemented in a first primer extension reaction according to the present disclosure, subcycling has been shown to improve on target rate (FIG. 8) and uniformity. The on-target rate is defined as defined as percent of quality filtered reads that match to the expected target which includes the first primer, insert sequences and reverse target specific primer where sequencing read length covers them. Example subcycling thermocycling programs for a first priming event and a second priming event are shown in Tables 3 and 4, respectively. Uniformity of the data was determined by identifying the percentage of targets that fell between 0.5× and 2.0× of the mean. Among 181 different targets, 130 of the targets (71.8%) had a normalized depth of between 0.5× and 2.0× of the mean. When measured as a function of amplicon GC content, among 181 different targets 146 of the targets (80.7%) had a normalized depth of between 0.5× and 2.0× of the mean.

TABLE 3

Subcycling thermal profile 1.

| Step | Description | Temp. (° C.) | Time (sec) |
|---|---|---|---|
| 1 | Initial Denaturation | 95 | 900 |
| 2 | Intermediate Temp | 80 | — |
| 3 | Annealing | 55 | — |
| 4 | Annealing low | 55 | 30 |
| 5 | Annealing high | 65 | 30 |
| | Repeat steps 4-5 (20x cycles) | | |
| 6 | Extension | 68 | 120 |
| 7 | End | 4 | Hold |

TABLE 4

Subcycling thermal profile 2.

| Step | Description | Temp. (° C.) | Time (sec) |
|---|---|---|---|
| 1 | Initial Denaturation | 98 | 60 |
| 2 | Denaturation | 98 | 10 |
| 3 | Intermediate Temp | 80 | — |
| 4 | Annealing | 55 | 30 |
| 5 | Annealing low | 55 | 30 |
| 6 | Annealing high | 65 | 30 |
| | Repeat steps 5-6 (4x cycles) | | |
| 7 | Extension | 68 | 30 |
| | Repeat steps 2-7 (5x cycles) | | |
| 8 | Denaturation | 98 | 10 |
| 9 | Annealing | 64 | 15 |
| 10 | Extension | 72 | 30 |
| | Repeat steps 8-10 (21x cycles) | | |
| 11 | End | 4 | Hold |

In Table 3, subcycling is included at steps 4 and 5, whereas in Table 4, subcycling is included at steps 5 and 6. Notably, Table 4 indicates a thermal cycling profile in which repetitions of steps 5 and 6 are nested within repetitions of steps 2-7. For example, a single cycle of steps 2-7 would include the following sequence of steps, in order: 2, 3, 4, 5, 6, 5, 6, 5, 6, 5, 6, 7.

Example 7: Gene Specific Primers with Complete Universal Adaptor

Figure 9:
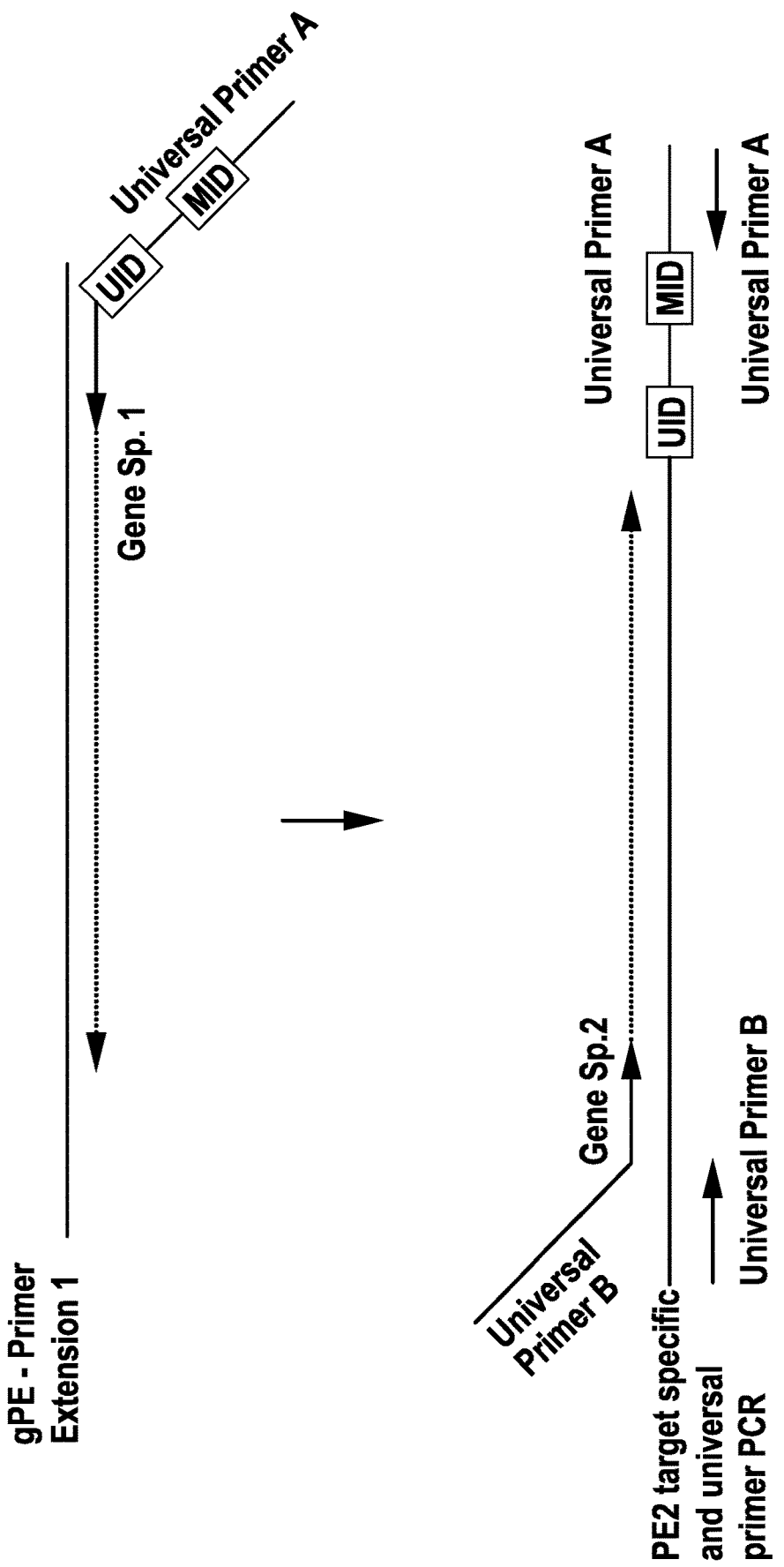
FIG. 9 is a schematic representation of an embodiment of a method according to the present disclosure including primers having both a UID and an MID incorporated therein.

In one aspect, it can be useful to generate gene specific primers (Gene Sp.1, UID, MID, Universal Primer A) with a universal adaptor, an index (MID) sequence, or a combination thereof. Referring to FIG. 9, the use of primers having one or both of a UID and an MID enables indexing of the first primer extension product during the first primer extension step of a method according to the present disclosure, thereby reducing the possibility of downstream cross-contamination, which can lead to false positive results.

Example 8 (Prophetic): Application of Primer Extension Target Enrichment to Droplet Digital PCR (ddPCR)

Figure 10:
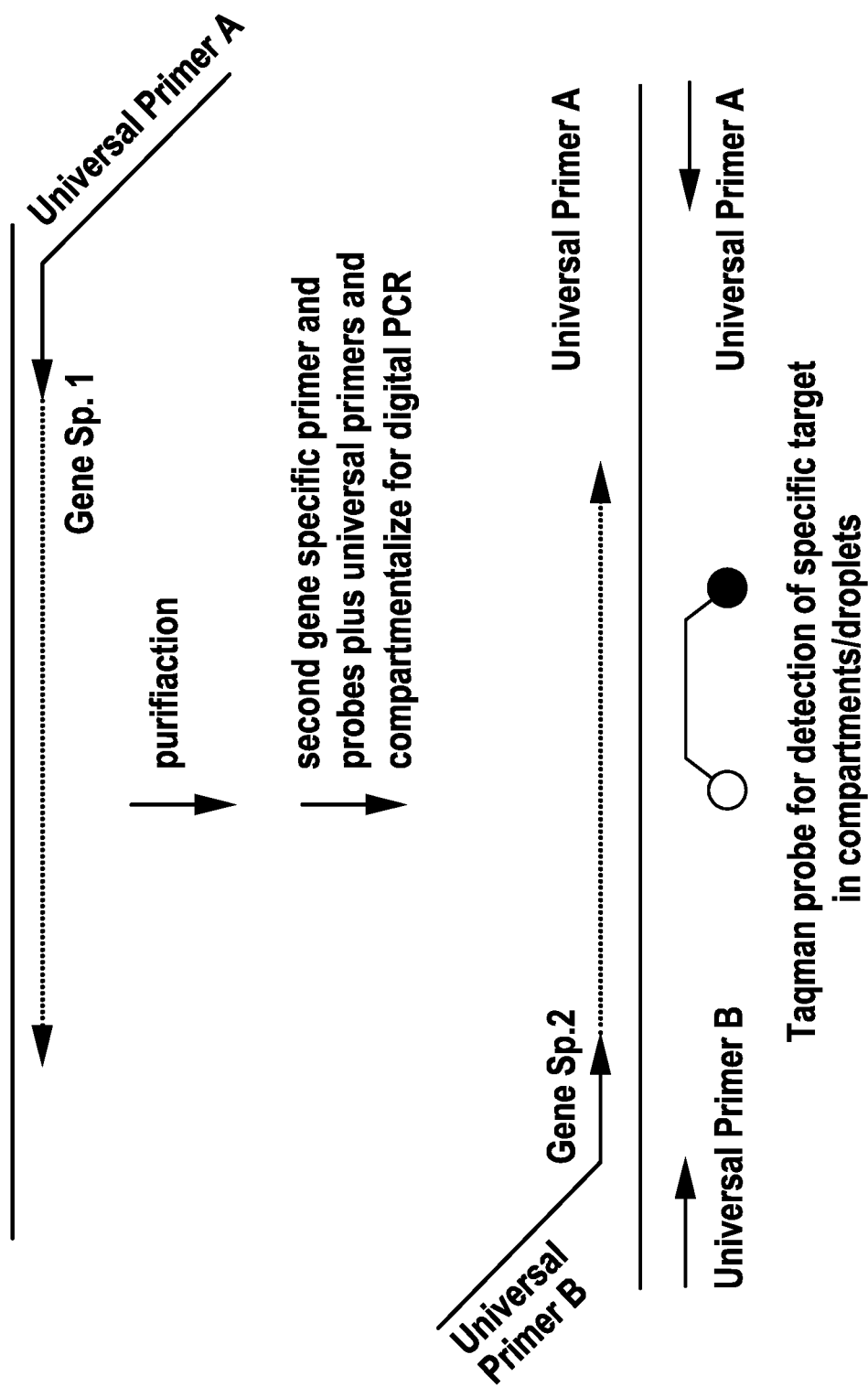
FIG. 10 is a schematic representation of an embodiment of a method according to the present disclosure in which the method is modified for use with digital droplet PCR (ddPCR).

Droplet digital PCR (ddPCR) is a method for performing digital PCR that is based on water-oil emulsion droplet technology. A sample is fractionated into thousands of droplets, and PCR amplification of the template molecules occurs in each individual droplet. With reference to FIG. 10, a method according to the present disclosure can be adapted for application to ddPCR. In one aspect, primers useful for ddPCR (e.g., a reverse primer and a universal primer) can be combined with a first primer extension product and exonuclease I. Notably, target enrichment by primer extension according to the present disclosure has the capabilities for highly multiplexed amplicon generation for next generation sequencing. Moreover, the methods can be applied to enable counting of target nucleic acids when used in ddPCR with a target-specific Taqman probe.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A kit for simultaneously enriching for DNA and RNA targets from samples comprising: (i) a first target-specific primer comprising a target-binding region specific to a sequence within a single-stranded RNA molecule and a region of complementarity to an adaptor; (ii) a reverse transcriptase; (iii) a second target-specific primer comprising a target-binding region specific to a sequence within a single-stranded DNA molecule and a region of complementarity to the adaptor; (iv) a DNA polymerase; (iv) the adaptor, wherein the adapter comprises a longer strand and a shorter strand, wherein the longer strand comprises a region complementary to the region in the first and second target-specific primers, and the shorter strand comprises a universal priming site; and (v) one or more universal primers; and wherein the kit further optionally comprises one or more reagents for DNA ligation, one or more reagents for DNA amplification, and/or one or more reagents for sequencing the enriched DNA and RNA targets.

2. The kit of claim 1, further comprising an exonuclease.

3. The kit of claim 2, wherein the exonuclease is exonuclease I.

4. The kit of claim 1, further comprising a Taqman probe.

* * * * *